(12) United States Patent
Tanna

(10) Patent No.: US 11,384,163 B2
(45) Date of Patent: Jul. 12, 2022

(54) ALKALI METAL SALT OF CARBOXYALKYL ETHER OF TAMARIND GUM WITH IMPROVED COMPOSITION

(71) Applicant: Raj Mahendra Tanna, Maharashtra (IN)

(72) Inventor: Raj Mahendra Tanna, Maharashtra (IN)

(73) Assignee: Raj Mahendra Tanna, Maharashtra (IN)

( * ) Notice: Subject to any disclaimer, the term of this patent is extended or adjusted under 35 U.S.C. 154(b) by 283 days.

(21) Appl. No.: 16/630,596

(22) PCT Filed: Nov. 9, 2019

(86) PCT No.: PCT/IB2019/059640
§ 371 (c)(1),
(2) Date: Jan. 13, 2020

(87) PCT Pub. No.: WO2021/033020
PCT Pub. Date: Feb. 25, 2021

(65) Prior Publication Data
US 2021/0403608 A1 Dec. 30, 2021

(30) Foreign Application Priority Data

Aug. 20, 2019 (IN) .............................. 201921033577

(51) Int. Cl.
*C08B 37/00* (2006.01)
(52) U.S. Cl.
CPC .............................. *C08B 37/0087* (2013.01)
(58) Field of Classification Search
CPC ................................................ C08B 37/0087
See application file for complete search history.

(56) References Cited

FOREIGN PATENT DOCUMENTS

| JP | 60166302 A | 8/1985 |
|---|---|---|
| JP | H0275602 A | 3/1990 |
| JP | 0299502 A | 4/1990 |
| WO | 2020/026041 A1 | 2/2020 |

OTHER PUBLICATIONS

Prabhanjan, H., Starch/Starke, 1989, 41(11) p. 409-414. (Year: 1989).*
Hamman et al., Current Pharmaceutical Design, 2015, 21, p. 4775-4797 (Year: 2015).*
Goyal et al.; "Carboxymethylation of Tamarind kernel powder"; Carbohydrate Polymers, vol. 69, Issue 2, Jun. 1, 2007, pp. 251-255; DOI:http://doi.org/10.1016/j. carbpol. 2006.10.001.
Mali et al.; "Extraction, Characterization and Functionalization of Tamarind Gum"; Research Journal of Pharmacy & Technology, pp. 1745-1752; vol. 12, Issue 4, Apr. 2019; DOI: 10.5958/0974-360X. 2019.00292.0.
Pal Sagar et al.; "Carboxy tamarind:Synthesis, characterization and its application as novel drug-delievery agent", Journal of Applied Polymer Science, vol. 110, No. 1, Oct. 5, 2008 (Oct. 5, 2008), pp. 392-400, XP05578694, US ISSN: 0021-8995, DOI:10.1002/app. 2845.

* cited by examiner

Primary Examiner — Jonathan S Lau
(74) Attorney, Agent, or Firm — Dickinson Wright PLLC

(57) ABSTRACT

The present disclosure relates to an alkali metal salt of carboxyalkyl ether of tamarind gum with low fat content and high protein content and other elements like carbon, hydrogen and nitrogen at desired concentration levels. The modified alkali metal salt of carboxyalkyl ether of tamarind gum with improved composition of the present disclosure possesses high viscosity, cold water solubility, and desired particle size and purity levels and is biodegradable.

5 Claims, 1 Drawing Sheet

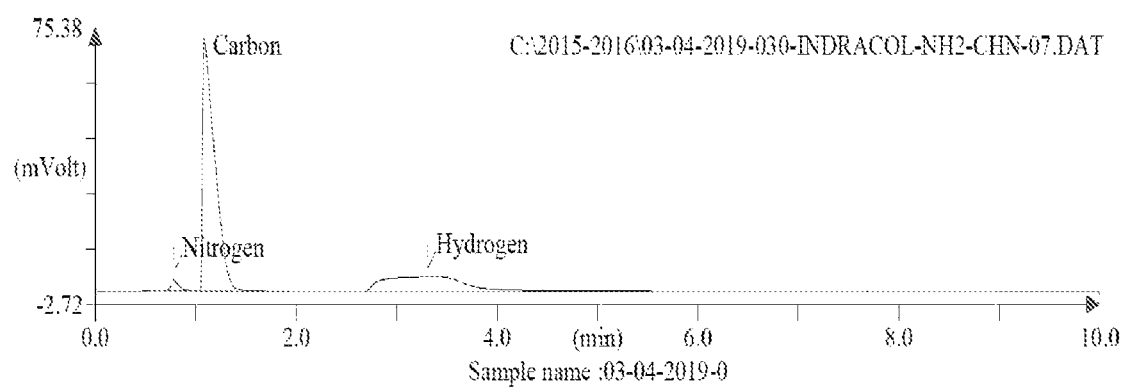

ALKALI METAL SALT OF CARBOXYALKYL ETHER OF TAMARIND GUM WITH IMPROVED COMPOSITION

FIELD OF THE INVENTION

The present disclosure relates to alkali metal salt of carboxyalkyl ether of tamarind gum with improved composition. More particularly the present disclosure relates to alkali metal salt of carboxyalkyl ether of tamarind gum with low fat and high protein content and desired concentration levels of other elements, viscosity and cold water solubility.

BACKGROUND OF THE INVENTION

Background description includes information that may be useful in understanding the present invention. It is not an admission that any of the information provided herein is prior art or relevant to the presently claimed invention, or that any publication specifically or implicitly referenced is prior art.

The Chemical industry with segments like textile chemicals, paint additives, paper manufacturing, home care, and personal care has significant environmental footprints. These segments persistently utilize hazardous materials and produce a significant amount of hazardous waste. The home and personal care industries, which heavily rely on specialty additives derived from petroleum starting point ingredients further add to environment degradation and pollution. Majority of the home and personal care formulations are heavily dependent on synthetic thickeners and rheology modifiers for example acrylate based polymers are derived from propylene which are fossil fuel by-products and hence do not fulfil criteria of sustainable sourcing and production. Many of these synthetic thickeners and rheology modifiers are very persistent in the environment as they are not biodegradable leading to high land and aquatic toxicity disrupting ecology cycles.

There have been several efforts to introduce naturally modified polymers for example cellulose ethers and modified guar gums. Though these are derived from natural sources the reaction and processing pathways are not the most sustainable. For example, polymers like hydroxy ethyl cellulose, hydroxy propyl cellulose are derivatives of cellulose which is derived from wood barks and plants and hence not offer sustainable solution. Other alternative raw materials like lignin a by-product of other industries too does not present a sustainable option, as such raw materials need to be processed using parameters not adequate to process in its entirety. Another, Concern is the harmful chemicals that are required in such process like ethylene oxide and propylene oxide. Ethylene oxide is toxic and exposure to high levels may cause significant harm, particularly to aquatic organisms. Ethylene oxide does not accumulate in the environment, but its breakdown in air and water is fairly slow as a volatile organic constituent that may be involved in the formation of ground level of ozone, which can damage crops and environment.

Another natural polymer that has been widely used in personal care products like cosmetics for example hair care formulations as well as in home care products, is guar gum, particularly cationic guar gum. One of the major shortcomings with cationic guar gum is that it cannot be desorbed completely from the hair. This means that shampoo formulations containing it tend to over condition the hair and to cause buildup and it is also difficult to remove, these are the most striking weaknesses of cationic guar gum based polymers. Besides, the cationic guar gum derivative due to synthetic cationic monomer is not biodegradable and hence it does not pass the Organisation for Economic Co-operation and Development (OECD) biodegradability guideline. Such limitations make cationic guar gum not a very favourable polymeric material.

Tamarind gum powder is another polymeric material with be promising potential for many industrial uses. It has been conventionally used in various industries as a thickening agent or stabilizer. The composition of tamarind gum obtained from seed kernel includes 15.4-22.7% protein, 3.0-7.4% Oil, 0.7-8.2% crude fiber, 65-72.2% non fiber carbohydrates, 2.45 to 3.3% ash on dry basis. Commercial Tamarind gum has a creamy white to light tan colour, with a fatty taste and odour and has tendency to lump and go rancid due to very high fat content (42.8 g/Kg). A much purer Tamarind seed polysaccharide (TSP) can be obtained by purification; however, the yield is only about 50% of the original tamarind gum.

One of the major drawbacks of tamarind gum is that it frequently does not disperse completely, and sols are usually turbid and contain suspended solid particles. Moreover, such sols are usually fairly viscous and accordingly incapable of filtration for removal of the suspended solids. Thus, tamarind gum with purity level suitable for various applications is desirable. Another problem with tamarind gum is that though it is cold water dispersible it is not cold water soluble and forms a sol with apparent high viscosity only after boiling the mixture for 20-30 min. This is cumbersome requires a higher lead time and it increases the processing cost in the textile industry.

To overcome problems such as purity, cold water solubility, fat percentage, lumpy nature, attempts have been made to functionally derivatize tamarind gum through chemical treatment with a variety of functional groups such as carboxymethyl, acetal, hydroxyl alkyl, thiol, polymer grafting, etc. One of the approaches is to chemically modify tamarind gum to either cationic or anionic form which have greater potential and give higher viscosities in certain conditions. One such modified form is carboxymethylation of tamarind gum to obtain an anionic form which could be a promising product for various applications. However, modification of products can have a negative impact on their apparent viscosities which is closely related to their degree of substitution. The viscosity of carboxymethylated form could be gained with increasing degree of substitution, however only up until a Degree of substitution of 0.08 DS, beyond which it drops. Further, increase in the DS also leads to the significant reduction in protein content and degradability. Several other modifications such as hydroxypropylation, cynoethylation, thiol functionalization, grafting with synthetic polymers like methylmethacrylate and crosslinking with epichlorohydrin etc. are tried however, such modifications have not been found to provide satisfactory derivatives, as such derivatives are either not safe for human consumption and would defeat the purpose of its functionalization for one of the prime application as promising excipient in the pharmaceutical industry or such modified forms of tamarind gums tend to have very low biodegradability posing harm to humans and environment.

There has been thus an unmet need to provide modified tamarind gum with low fat content, desired viscosity, controlled particle size and purity levels suitable for various applications, flow rheology, cold water solubility, while retaining some of the characteristic of native gum like nitrogen, carbon, hydrogen contents and biodegradability rendering it suitable and safe for human consumption and environment friendly to reduce ecological burden.

OBJECTS OF THE INVENTION

It is an object of the present disclosure to provide a alkali metal salt of carboxyalkyl ether of tamarind gum with improved composition.

It is one more object of the present disclosure to provide modified alkali metal salt of carboxyalkyl ether of tamarind gum with low fat and high protein content and desired concentration levels of other elements.

It is another object of the present disclosure to provide modified alkali metal salt of carboxyalkyl ether of tamarind gum with high viscosity, cold water solubility, and desired particle size and purity levels.

It is a further object of the present disclosure to provide modified alkali metal salt of carboxyalkyl ether of tamarind gum which is biodegradable.

SUMMARY OF THE INVENTION

In an aspect the present disclosure provides an alkali metal salt of carboxyalkyl ether of tamarind gum with improved composition.

In an aspect the present disclosure provides a alkali metal salt of carboxyalkyl ether of tamarind gum with low fat and high protein content and desired concentration levels of other elements like carbon, hydrogen, and nitrogen.

In an aspect the present disclosure provides alkali metal salt of carboxyalkyl ether of tamarind gum with high viscosity, cold water solubility, and desired particle size and purity levels.

In an aspect the present disclosure provides alkali metal salt of carboxyalkyl ether of tamarind gum which is biodegradable.

In an aspect the present disclosure provides alkali metal salt of carboxyalkyl ether of tamarind gum with improved composition comprising fat content ranging from about 0.1% to about 2%, preferably, from about 0.15% to 1%; protein content ranging from about 13% to about 18%; salt content ranging from about 0.25% to about 1.85%; nitrogen content at least 2%, preferably ranging from about 2% to about 2.5%; carbon content about 41.5%; hydrogen content about 6.632% on wt./wt. basis and said alkali metal salt of carboxyalkyl ether of tamarind gum with improved composition is cold water soluble and has viscosity value 7000 cps to 150000 cps at 30 Deg C. and 20 rpm stirring. The particle size of the modified alkali metal salt of carboxyalkyl ether of tamarind gum with improved composition is in the range of about 50 to 150 microns. The modified alkali metal salt of carboxyalkyl ether of tamarind gum with improved composition as per the present disclosure exhibits improved rheology as compared to conventional tamarind gum and does not show rancidity over a period of storage.

In an aspect the present disclosure provides modified alkali metal salt of carboxyalkyl ether of tamarind gum with improved composition suitable as a thickener, flow rheology modifier, viscosity enhancer, retention aid, stabilizer, anti-reposition polymer, solubilizer, binding agent, defoamer, emulsion stabilizer and importantly gelling or erodible polymer, which is biodegradable and thus the most be fitting candidate for many industrial applications for example in cosmetic industry in personal care and toiletry products for example hair care products, home care industry for example in detergents and toilet cleaners, in textile industry for printing applications, paint industry, paper and pulp industry, ceramic industry, auto care formulation segment and many more.

Various objects, features, aspects and advantages of the inventive subject matter will become more apparent from the following detailed description of preferred embodiments.

BRIEF DESCRIPTION OF THE ACCOMPANYING DRAWING

Characteristics and advantages of the subject matter as disclosed in the present disclosure will become clearer from the detailed description of an embodiment thereof, with reference to the attached drawing, given purely by way of an example, in which:

FIG. 1 is a chromatography graph showing peaks corresponding to nitrogen, carbon and hydrogen confirming presence of these elements.

DETAILED DESCRIPTION OF THE INVENTION

The following is a detailed description of embodiments of the disclosure depicted in the accompanying drawings. The embodiments are in such detail as to clearly communicate the disclosure. However, the amount of detail offered is not intended to limit the anticipated variations of embodiments; on the contrary, the intention is to cover all modifications, equivalents, and alternatives failing within the spirit and scope of the present disclosure as defined by the appended claims.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Unless the context requires otherwise, throughout the specification which follow, the word "comprise" and variations thereof, such as, "comprises" and "comprising" are to be construed in an open, inclusive sense that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable.

The recitation of ranges of values herein is merely intended to serve as a shorthand method of referring individually to each separate value falling within the range. Unless otherwise indicated herein, each individual value is incorporated into the specification as if it were individually recited herein.

All processes described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

The headings and abstract of the invention provided herein are for convenience only and do not interpret the scope or meaning of the embodiments.

The following discussion provides many example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability.

It should also be appreciated that the present disclosure can be implemented in numerous ways, including as a method or a system. In this specification, these implementations, or any other form that the invention may take, may be referred to as processes. In general, the order of the steps of the disclosed processes may be altered within the scope of the invention.

Various terms are used herein and claimed. To the extent a term used in a claim is not defined below, it should be given the broadest definition persons in the pertinent art have given that term as reflected in printed publications and issued patents at the time of filing.

Reference will now be made in detail to the exemplary embodiments of the present disclosure, examples of which are illustrated in the accompanying drawings.

The description that follows, and the embodiments described therein, is provided by way of illustration of an example, or examples, of particular embodiments of the principles and aspects of the present disclosure. These examples are provided for the purposes of explanation, and not of limitation, of those principles and of the disclosure.

The present disclosure relates to an alkali metal salt of carboxyalkyl ether of tamarind gum with improved composition.

In general embodiments the present disclosure provides a modified alkali metal salt of carboxyalkyl ether of tamarind gum with low fat and high protein content and desired concentration levels of other elements like carbon, hydrogen, and nitrogen. The modified alkali metal salt of carboxyalkyl ether of tamarind gum with improved composition of the present disclosure possesses high viscosity, cold water solubility, and desired particle size and purity levels and is biodegradable.

In one embodiment the present disclosure provides the modified metal salt of carboxymethyl ether of tamarind gum with improved composition low fat and high protein content and desired concentration levels of other elements like carbon, hydrogen, and nitrogen; desired viscosity, rheology, cold water solubility and better biodegradability as compared to other artificial derivatives of tamarind gum. The modified metal salt of carboxymethyl ether of tamarind gum with improved composition of the present disclosure possesses desired moisture content, reduced ash content, better stability in O/W emulsion and other physicochemical properties.

In an embodiment the present disclosure provides modified alkali metal salt of carboxyalkyl ether of tamarind gum with improved composition comprising fat content ranging from about 0.1% to about 2%, preferably, from about 0.15% to 1%; protein content ranging from about 13% to about 18%; salt content ranging from about 0.25% to about 1.85%; nitrogen content at least 2%, preferably ranging from about 2% to about 2.5%; carbon content about 41.5%; hydrogen content about 6.632% on wt/wt. basis. The modified metal salt of carboxymethyl ether of tamarind gum with improved composition is cold water soluble and has viscosity value 7000 cps to 150000 cps at 30 Deg. C and 20 rpm stirring. The particle size of the modified alkali metal salt of carboxyalkyl ether of tamarind gum with improved composition is in the range of about 50 to 150 microns.

In one embodiment, the particle size of the modified alkali metal salt of carboxyalkyl ether of tamarind gum with improved composition is in the range of about 50 to 60 microns, preferably at least 90% passing through 100 mesh to at least 85% passing through 50 mesh sieve. The modified alkali metal salt of carboxyalkyl ether of tamarind gum with improved composition as per the present disclosure exhibits improved rheology as compared to conventional tamarind gum. The alkali metal salt of carboxyalkyl ether of tamarind gum with improved composition as per the present disclosure exhibits better stability over a longer duration as it does not become rancid and yet biodegradable.

The modified alkali metal salt of carboxyalkyl ether of tamarind gum with improved composition is suitable as a thickener, flow rheology modifier, viscosity enhancer, retention aid, stabilizer, anti-reposition polymer, solubilizer, binding agent, defoamer, emulsion stabilizer and importantly gelling or erodible polymer, which is biodegradable and thus the most be fitting candidate for many industrial applications.

The exemplary applications of the modified alkali metal salt of carboxyalkyl ether of tamarind gum with improved composition of the present disclosure owing to its composition and characteristics include use in a printing paste for good reproducibility of the printing results; in paint formulation for providing excellent pseudo plastic flow rheology and thickener; in cosmetic formulations as an effective stabilizer, emulsifier, rheology aid and thickener; in auto care formulations as a oil in water emulsifier and emulsion stabiliser; in paper industry as a burst factor and retention aid; in home care formulations as a bio-degradable acid thickener, emulsifier and rheology modifier; in detergent formulations as an anti-reposition polymer; in tile adhesive formulations as a shear strength improver; as a solubilizer and thickener for strong reducing agents; in ceramic industry as an effective binding agent; as a defoamer in preparation of textile auxiliaries, and as a bio-degradable polymer replacement for acrylic acid based thickeners in textile printing.

The modified alkali metal salt of carboxyalkyl ether of tamarind gum with improved composition of the present disclosure owing to its composition and characteristics satisfies the existing needs, as well as others, and generally overcomes the deficiencies found in the existing art.

While the foregoing description discloses various embodiments of the disclosure, other and further embodiments of the invention may be devised without departing from the basic scope of the disclosure. The invention is not limited to the described embodiments, versions or examples, which are included to enable a person having ordinary skill in the art to make and use the invention when combined with information and knowledge available to the person having ordinary skill in the art.

The present disclosure is further explained in the form of following example. However, it is to be understood that the foregoing example is merely illustrative and is not to be taken as limitations upon the scope of the invention. Various changes and modifications to the disclosed embodiments will be apparent to those skilled in the art. Such changes and modifications may be made without departing from the scope of the invention.

Example 1

Process for Preparing Sodium Salt of Carboxymethyl Ether of Tamarind Gum with High Protein and Low Fat Content and Characterization:

Marketed tamarind gum powder was procured from commercial vendor and was tested for chemical composition: carbohydrate content about 69.43%, protein content about 19.23%, oil content about 6.64%, salt content about 2.46%, and crude fiber content about 2.2%. Tamarind gum powder was then passed through sieves of different mesh size to have more than 90% passing through sieve of 270 mesh to 300 mesh. Tamarind gum powder with such particle size (1 KG) was added to the mixture containing methyl alcohol (3 Kg), sodium hydroxide (40 Grams), and hydrogen peroxide (0.2 g Gram) in a reaction vessel, and the alkaline mercerization was carried out at 58° C. A high speed shearing agitation apparatus with having shearing propeller blades was disposed in the reaction vessel, and during the mercerization step, the starting tamarind gum was sufficiently agitated for 120 minutes to transform the tamarind gum powder to a slurry of the tamarind gum-alkali in methyl alcohol, an etherifying agent, i.e. sodium monochloroacetate (80 Grams), was added to the obtained tamarind gum-alkali slurry, and the temperature was elevated above 60° C., but less than 100° C., preferably at 60° C. to 80° C., and the etherification was carried out for 180 minutes to provide sodium salt of carboxymethyl ether of tamarind gum. Thus, obtained sodium salt of carboxymethyl ether of tamarind gum was separated from the reaction mixture with the help of centrifuge by carrying out centrifugation at 400 RPM to 800 RPM for 15-30 minutes. The separated sodium salt of carboxymethyl ether of tamarind gum was dried in a vacuum dryer at 35° C. to 75° C. The dried powder obtained was blended in blender for example in conical blender for about 60-90 minutes to obtain uniform powder of sodium salt of carboxymethyl ether of tamarind gum, which was then passed through sieve of 270 mesh to provide uniform powder of sodium salt of carboxymethyl ether of tamarind gum with more than 92% of the powder having particle size of 50-60 microns. The yield obtained was more than 95% of the starting material. The sodium salt of carboxymethyl ether of tamarind gum thus obtained was found to have degree of substitution of about 0.01, it was subjected to various testing and analysis to check characteristics like fat content, protein content, salt content, viscosity. CHNS elements content, moisture content, cold water solubility, heavy metal content, and biodegradability.

Characterization Studies:

A. Comparative Determination of Fat, Protein and Salt Contents of the Sodium Salt of Carboxymethyl Ether of Tamarind Gum of the Present Invention and the Marketed Sample:

The sample of sodium salt of carboxymethyl ether of tamarind gum as prepared above and the marketed sample of the conventionally prepared sodium salt of carboxymethyl ether of tamarind gum were subjected to fat content, protein (NC6.25) content and salt content. The protocols used and findings of the analyses are reported in Table 1 as follows:

TABLE 1

| | | Results | |
| --- | --- | --- | --- |
| Tests | Protocol | Present Invention | Marketed |
| Fat Content | IS 7874 (P.I): 1975 | 0.16% | 4.92% |
| Protein Content | IS 7874 (P.I): 1975 | 17.96% | 13.89% |
| Salt Content | IS 7874 (P.II): 1975 | 0.27% | 1.80% |

B. Viscosity Determination of the Sodium Salt of Carboxymethyl Ether of Tamarind Gum with Low Fat and High Protein Content of the Present Invention and the Marketed Sample:

Viscosity of samples of the sodium salt of carboxymethyl ether of tamarind gum obtained as per the present invention and the marketed sample were determined using the Brookfield Viscometer by employing techniques in viscometry. By measuring viscosity through the varying flow conditions of the sample material tested. Viscosity of 8% solution of sample of the sodium salt of carboxymethyl ether of tamarind gum obtained as per the present invention was tested at 20 rpm, 30° C. Viscosity of 10% solution of the marketed sample of sodium salt of carboxymethyl ether of tamarind gum was tested at 10 rpm, 30° C.

Results are reported as follows:

a. Viscosity of the sodium salt of carboxymethyl ether of tamarind gum with low fat and high protein content as per the present invention: 130,000 cps.

b. Viscosity of the marketed sample of the sodium salt of carboxymethyl ether of tamarind gum: 4,000 cps.

The above results clearly show that the sodium salt of carboxymethyl ether of tamarind gum with low fat and high protein content as per this example showed much superior viscosity of more than 130,000 cps at 20 rpm, 30° C. (Brookfield) as compared to the conventional sodium salt of carboxymethyl ether of tamarind gum exhibiting only around 4000 cps at 10 rpm, 30° C. in a 10% solution (Brookfield). These results in turn indicate much superior rheology of the sodium salt of carboxymethyl ether of tamarind gum obtained as per this example as compared with the marketed sample.

C. CHNS Content Determination:

The sodium salt of carboxymethyl ether of tamarind gum with low fat and high protein content as per the present disclosure was subjected to CHNS analysis for determining the percentages of Carbon, Hydrogen, Nitrogen, Sulphur and Oxygen of organic compounds, using "Dumas method" by complete and instantaneous oxidation of the sample by "flash combustion" using CHNS(O) Analyzer of "FLASH EA 1112" series made by Thermo finnigan, Italy. The instrument was calibrated with the analysis of std compounds using the K-factors calculations. The combustion products were separated by a chromatographic column and detected by the thermal conductivity detector (T.C.D.), providing an output signal proportional to the concentration of the individual components of the mixture. Based on the output graph (FIG. 1) the percentage of nitrogen, carbon and hydrogen in the same of the sodium salt of carboxymethyl ether of tamarind gum with low fat and high protein content of the present disclosure is reported in Table 2 as follows:

TABLE 2

| Peak Number (#) | Retention Time (min) | Area (.1*uV*sec) | Element % | Component |
| --- | --- | --- | --- | --- |
| 1 | 0.783 | 182328 | 2.478 | Nitrogen |
| 2 | 1.092 | 6029384 | 41.468 | Carbon |
| 3 | 3.308 | 2624468 | 6.632 | Hydrogen |

D. Moisture Content:

Moisture contents of the sample of the sodium salt of carboxymethyl ether of tamarind gum with low fat and high protein content as per the present disclosure was determined according to APHA 2540 E. Result is provided as below:
Moisture Content: 5.65%

E. Cold Water Solubility:

The sample of the sodium salt of carboxymethyl ether of tamarind gum with low fat and high protein content as per the present disclosure was dissolved in cold water. The sample dissolved completely, proving its solubility in cold water.

F. Heavy Metal Analysis:

The sample of the sodium salt of carboxymethyl ether of tamarind gum with low fat and high protein content as per the present disclosure was analyzed for detection of the heavy metals considered to be harmful to the human beings according to EPA 3051 using microwave digestion analysis on ICP-OES; detection limit was 1.0 mg/kg. Results are provided in following Table 3.

TABLE 3

| Sr. No | Name of Heavy Metal | Concentration (mg · kg) |
| --- | --- | --- |
| 1. | Arsenic (As) | Not detected |
| 2. | Lead (Pb) | Not detected |
| 3. | Cadmium (Cd) | Not detected |
| 4. | Mercury (Hg) | Not detected |
| 5. | Cobalt (Co) | Not Detected |

TABLE 3-continued

| Sr. No | Name of Heavy Metal | Concentration (mg · kg) |
| --- | --- | --- |
| 6. | Antimony (Sb) | Not Detected |
| 7. | Tin(Sn) | Not Detected |

The above results prove that the sodium salt of carboxymethyl ether of tamarind gum with low fat and high protein content as per the present disclosure does not contain harmful heavy metals and is safe for applications for human use.

G. Biodegradability:

The sample of sodium salt of carboxymethyl ether of tamarind gum of the present disclosure was further examined to assess it's biodegradability by different methods as follows:

a. Test for Inherent Biodegradability:
The sample was subjected to inherent biodegradability test according to OECD 302 B (Zahn Wellens test) method for the period of 28 days. Finding of this study is reported below:
Inherent Biodegradability: 90% b. Test for Ready Biodegradability:
The sample was subjected to ready biodegradability test according to OECD 301 F Manometric Respirometry test method. Finding of this study is reported below:
Ready Biodegradability: 86%

The above tests result clearly show that the metal salt of carboxymethyl ether of tamarind gum with improved composition as per the present disclosure comprises low fat content; high protein content; along with elements like carbon, hydrogen and nitrogen at desired concentration levels; desired salt and moisture content, heavy metal levels safe for humans, better viscosity, rheology, cold water solubility, not rancid over a period of time, better stability, and better biodegradability thus rendering it suitable for diverse applications including those involving use for humans.

I claim:

1. An alkali metal salt of carboxyalkyl ether of tamarind gum with composition comprising nitrogen content of 2% to 2.5%; carbon content of 41.5%; hydrogen content of 6.632%, low fat content in the range of 0.1% to 2%; and high protein content in the range of 13% to 18% on wt./wt. basis.

2. The alkali metal salt of carboxyalkyl ether of tamarind gum with composition as claimed in claim 1, wherein the modified alkali metal salt of carboxyalkyl ether of tamarind gum with composition is biodegradable.

3. The alkali metal salt of carboxyalkyl ether of tamarind gum with composition as claimed in claim 1 wherein, the modified alkali metal salt of carboxyalkyl ether of tamarind gum with composition is cold water soluble.

4. The alkali metal salt of carboxyalkyl ether of tamarind gum with composition as claimed in claim 1 wherein, the modified alkali metal salt of carboxyalkyl ether of tamarind gum with composition has viscosity value 7000 cps to 150,000 cps.

5. The alkali metal salt of carboxyalkyl ether of tamarind gum with composition as claimed in claim 1 wherein, the average particle size of the modified alkali metal salt of carboxyalkyl ether of tamarind gum with composition is in the range of about 100 to 180 mesh.

* * * * *